(12) United States Patent
Pryor et al.

(10) Patent No.: US 8,882,685 B2
(45) Date of Patent: Nov. 11, 2014

(54) APPARATUS AND METHODS FOR PHOTOTHERAPY

(75) Inventors: Brian Pryor, Ewing, NJ (US); Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 1302 days.

(21) Appl. No.: 12/127,085

(22) Filed: May 27, 2008

(65) Prior Publication Data
US 2009/0299236 A1   Dec. 3, 2009

(51) Int. Cl.
| A61H 15/02 | (2006.01) |
| A61H 1/00 | (2006.01) |
| A61H 15/00 | (2006.01) |
| A61N 5/067 | (2006.01) |
| A61B 18/20 | (2006.01) |
| A61N 5/06 | (2006.01) |
| A61B 18/00 | (2006.01) |

(52) U.S. Cl.
CPC ...... *A61H 15/0092* (2013.01); *A61N 2005/067* (2013.01); *A61B 18/203* (2013.01); *A61N 2005/0651* (2013.01); *A61N 5/0619* (2013.01); *A61N 2005/0644* (2013.01); *A61N 2005/063* (2013.01); *A61H 2201/5071* (2013.01); *A61H 2201/10* (2013.01); *A61B 2018/00452* (2013.01); *A61H 2015/0064* (2013.01); *A61B 2018/0047* (2013.01); *A61N 5/0616* (2013.01)
USPC ............... 601/19; 601/15; 601/113; 601/131

(58) Field of Classification Search
CPC .............. A61H 15/00; A61H 15/0078; A61H 15/0085; A61H 15/0092; A61H 15/02; A61H 2015/0007; A61H 2015/0042; A61H 2015/005; A61H 2015/0064; A61H 2015/0071
USPC .......... 601/15, 18–22, DIG. 5, 113, 128, 129, 601/131, 132; 607/88–95, 80
See application file for complete search history.

(56) References Cited

U.S. PATENT DOCUMENTS

| 1,844,247 | A |  | 2/1932 | Freemon |  |
| 2,183,726 | A | * | 12/1939 | Sommer et al. | 601/17 |
| 2,490,074 | A |  | 12/1949 | Marty |  |
| 2,699,771 | A |  | 1/1955 | Ruttger-Pelli |  |
| 5,336,159 | A |  | 8/1994 | Cheng |  |
| 6,056,204 | A |  | 5/2000 | Glezer et al. |  |
| 6,063,108 | A |  | 5/2000 | Salansky et al. |  |
| 6,066,129 | A |  | 5/2000 | Larson |  |
| 6,214,035 | B1 |  | 4/2001 | Streeter |  |
| 6,413,268 | B1 |  | 7/2002 | Hartman |  |
| 6,866,678 | B2 |  | 3/2005 | Shenderova et al. |  |
| 7,033,382 | B2 |  | 4/2006 | Lach |  |
| 7,083,580 | B2 |  | 8/2006 | Bernabei |  |
| 7,144,247 | B2 | * | 12/2006 | Black | 433/29 |
| 7,264,598 | B2 |  | 9/2007 | Shin |  |
| 7,282,037 | B2 |  | 10/2007 | Cho |  |
| 7,335,170 | B2 | * | 2/2008 | Milne et al. | 601/15 |
| 7,749,178 | B2 |  | 7/2010 | Imboden et al. |  |
| 7,762,964 | B2 | * | 7/2010 | Slatkine | 601/7 |

(Continued)

*Primary Examiner* — Valerie L Skorupa
(74) *Attorney, Agent, or Firm* — Fish & Richardson P.C.

(57) ABSTRACT

There is provided a phototherapy apparatus, in which the therapeutic light is delivered through one or more massage components. The massage component provides mechanical massage to the subject biological tissue and modifies the properties of the subject tissue in thickness, density, etc. to facilitate the absorption of the therapeutic light and enhance the effect of the phototherapy procedure. The light source of the phototherapy apparatus is actively cooled by a synthetic jet cooler.

15 Claims, 1 Drawing Sheet

(56) References Cited

U.S. PATENT DOCUMENTS

| | | |
|---|---|---|
| 2003/0163068 A1* | 8/2003 | Kang ............................. 601/15 |
| 2003/0232303 A1 | 12/2003 | Black |
| 2004/0138727 A1 | 7/2004 | Taboada et al. |
| 2004/0193235 A1 | 9/2004 | Altshuler et al. |
| 2004/0193236 A1 | 9/2004 | Altshuler et al. |
| 2004/0236252 A1 | 11/2004 | Muzzi et al. |
| 2004/0260209 A1 | 12/2004 | Ella et al. |
| 2004/0260212 A1* | 12/2004 | Cho ............................... 601/15 |
| 2006/0235494 A1 | 10/2006 | Vanderschuit |
| 2006/0253051 A1 | 11/2006 | Milne et al. |
| 2007/0073366 A1 | 3/2007 | Porco |
| 2007/0096118 A1* | 5/2007 | Mahalingam et al. .......... 257/81 |
| 2008/0014011 A1* | 1/2008 | Rossen ......................... 401/195 |
| 2008/0262394 A1 | 10/2008 | Pryor et al. |
| 2009/0001372 A1* | 1/2009 | Arik et al. ....................... 257/58 |
| 2009/0234253 A1* | 9/2009 | Vandenbelt et al. ............ 601/15 |
| 2011/0144725 A1 | 6/2011 | Pryor et al. |

* cited by examiner

APPARATUS AND METHODS FOR PHOTOTHERAPY

FIELD OF THE INVENTION

This invention relates to apparatus and methods for phototherapy.

BACKGROUND

Phototherapy relates to treatment of biological tissues, such as skin tissues, using visible, ultraviolet, and/or infrared lights. The light treatment may be applied solely for sterilization, pain relief, bio-modulation, and photo-rejuvenation. Alternatively, the treatment may be used in combination with certain photo-sensitive drugs or nutrition supplements. In comparison with laser surgery, the light intensity employed in phototherapy is much lower. Thus the light sources used in phototherapy are not limited to lasers but may include light emitting diodes (LEDs) and/or certain types of lamps as well. Typical applications of phototherapy include wound healing, cellulite reduction, skin rejuvenation, pain relief, fat reduction and contouring, laser acupuncture, pressure ulcer treatment, etc.

It is well known in the prior art that phototherapy may be applied in combination with mechanical massage. Some examples can be found in U.S. Pat. No. 7,033,382 to Lach; and U.S. Patent Application Nos. 20060253051 to Milne et al, 20060235494, 20040236252 to Muzzi et al, and 20070073366 to Porco. However, none of the prior art suggests to apply phototherapy with mechanical massage in a concerted manner, where phototherapy and mechanical massage are applied to the same target area and benefit from each other thereby producing significantly improved therapeutic results. Furthermore, none of the prior art discloses a compact phototherapy/massage wand design, which provides effective heat dissipation for the high power lasers/LEDs yet maintains a small size and weight that can be easily handled by the practitioner.

SUMMARY OF THE INVENTION

According to one aspect of the present invention, there is provided a phototherapy apparatus, wherein the therapeutic light is delivered through one or more massage components. The massage component provides mechanical massage to a subject biological tissue and modifies the properties of the subject tissue in thickness, density, local pressure, microcirculation, etc. to facilitate the absorption and interaction of the therapeutic light with the subject tissue and enhance the effect of the phototherapy procedure. Meanwhile, the therapeutic light in its interaction with the illuminated tissue also facilitates and enhances the effect of the mechanical massage.

According to another aspect of the present invention, a piezoelectric based synthetic jet actuator is utilized to provide efficient thermal management for the light source of the phototherapy apparatus. The synthetic jet actuator features extremely low noise, low power consumption, and greatly extended lifetime.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1A:
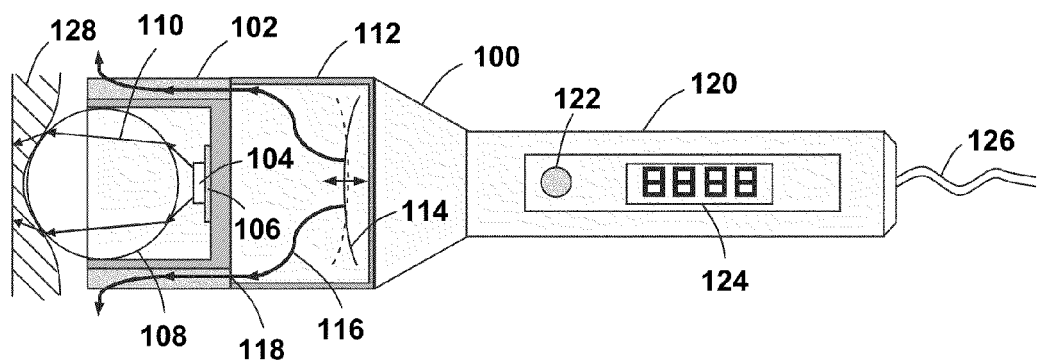
FIG. 1a illustrates a cross section view of one exemplified embodiment of the phototherapy apparatus, in which the therapeutic light is delivered through a transparent massage ball.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to phototherapy. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 1B:
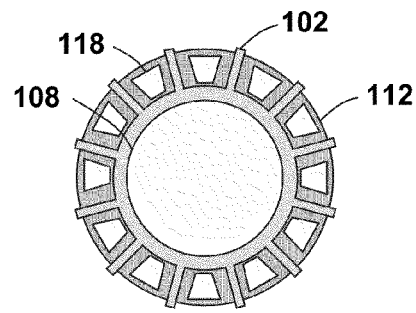
FIG. 1b illustrates a top view of the phototherapy apparatus of FIG. 1a from the side of the massage ball.

In the first embodiment of the present invention as shown in FIG. 1a and FIG. 1b, the phototherapy apparatus 100 is in the form of a phototherapy/massage wand comprising an optical head 102, a synthetic jet cooler 112, and a handle 120. The optical head 102 holds a laser or light emitting diode (LED) light source 104 and a rolling massage ball 108. The massage ball 108 may rotate freely in all directions (a 360° freedom of movement) in the optical head 102 with controlled friction. The massage ball 108 is transparent at the wavelength of the therapeutic light 110 that is produced by the light source 104. Thus the therapeutic light 110 can transmit through the massage ball 108 to the subject biological tissue 128 to be treated. It is also possible to incorporate a group of optical elements between the light source 104 and the massage ball 108 for controlling the divergence angle, intensity distribution, uniformity, beam size, etc. of the therapeutic light 110. The light source 104 is preferably a high power semiconductor laser or LED, such as a class IV semiconductor laser mounted on a thermal conductive substrate 106. The substrate 106 is further mounted on the optical head 102, which is also made of thermal conductive material and comprises an array of fins along its outer circumference for dissipating the heat produced by the light source 104.

The optical head 102 is mechanically coupled with a synthetic jet cooler 112, which comprises a piezoelectric actuator 114 and an array of ventilation holes 118 matching with the array of fins of the optical head 102. The periodic vibration of the piezoelectric actuator 114 produces a periodic jet of air flow 116 through those ventilation holes 118, which carries away the heated air around the circumference of the optical head 102. Comparing with conventional fans, this synthetic jet cooler is more efficient since the jet of air flow can be accurately directed toward the hot spot. In addition, the synthetic jet cooler offers much lower noise level, lower power consumption, and greatly extended lifetime.

The handle 120 of the phototherapy apparatus 100 comprises a group of control buttons 122 and a display unit 124 used to control and displays the on/off status and power level of the light source 104. The control buttons 122 and the display unit 124 are electrically connected to a drive/control circuit board (not shown) contained in the handle 120, which provides electric power and control signal to the light source 104 and the piezoelectric actuator 114. The drive/control circuit board is further powered through a wire 126 connected to a wall plug (not shown). In a slight variation of the present embodiment, the drive/control circuit board may be powered by batteries or rechargeable batteries.

Through the handle 120, a practitioner can applied a force to the massage ball 108, causing it to roll on the subject biological tissue 128 (such as skin tissue) and deliver a pressure on the tissue in contact with the massage ball 108. On one hand, this rolling and kneading action causes an increase in blood circulation and fluid mobilization of the subcutaneous tissue, smoothes and firms the subject anatomy. Thus lipolysis is restored and fat cell metabolism is reactivated, resulting in the reduction of fat tissue and smoothing of cellulite. It also can help for the relief of muscle aches and pain. On the other hand, the action also causes a reduction in tissue thickness and an increase in tissue density. This change in tissue property helps to reduce the overall absorption and scattering loss of the therapeutic light 110 and allows the therapeutic light 110 to penetrate deeper into the tissue and induce stronger photochemical processes, e.g. increase of ATP (adenosine triphosphate), triggering of photo neurological response and activation of enzymes, changes in local pressure, increases in temperature and permeability of cellular membranes. Since the massage ball 108 is in contact with the subject tissue 128, the therapeutic light 110 will penetrate into the subject tissue 128 directly with no air interface. This feature allows the practitioner to control the intensity of the delivered therapeutic light in a more accurate manner. The photo bio-modulation in turn helps to enhance the effect of the mechanical massage by stimulating inter or intra cellular response, increasing micro-circulation, etc.

In another variation of the present embodiment, the massage ball may have a diffusive or scattering optical surface, which is capable of spreading the transmitted light into various angles and directions. The diffusive surface can be prepared by forming some type of micro-structures or by coating a layer of diffusive optical material on the surface of the massage ball. When the massage ball is not in contact with the subject tissue, the therapeutic light is diffused by the diffusive surface as it transmits from the massage ball into air. Thus the transmitted light has an increased spread angle and hence a reduced light intensity when viewed from a distance away. This reduction in viewed light intensity enhances the safety level of the phototherapy apparatus. In comparison, when the massage ball is in contact with the subject tissue, the transmitted light is much less distorted or spread. This is due to the fact that the tissue in contact with the surface of the massage ball serves as an optical index matching medium which effectively reduces diffusing or scattering cause by the massage ball surface. Hence, the light beam is effectively delivered into the tissue with desired direction, angle, power density, depth, and intensity distribution. As another variation, certain optical index matching liquids, gels, suspension particles, powders may be applied between the massage ball and the subject tissue to further enhance light transmittance and reduce the light distortion caused by the massage ball surface. Those optical index matching media may also have therapeutic or pharmaceutical effect to further improve the effect of phototherapy.

In yet another variation of the present embodiment, the massage ball (or simply an optical window with curved surface) is rigidly affixed to the optical head and moves together or in unison with the optical head. In this variation, the mechanical massage is performed by kneading the subject tissue with the massage ball without the rolling action.

In yet another variation of the present embodiment, a motor is installed in the optical head and mechanically coupled to the massage ball to generate rolling, kneading, and/or vibration movements of the massage ball.

One application of the phototherapy apparatus 100 is relieving the pain associated with migraine headaches, in which therapeutic light is delivered through the transparent massage ball to the forehead, temples, paranasal sinus, and/or neck of the patient. The optical properties of the massage ball, such as its refractive index, diameter or curvature, etc. can be utilized to shape the light beam to an ideal spot size or value. The phototherapy apparatus 100 may further comprise a touch sensor or a pressure sensor (both not shown), such as a spring loaded device feature to control the on/off status of the light source in such a way that the light source can only be turned on when the massage ball touches the skin tissue. This helps to improve the safety of laser treatments around the eye by limiting the chance of laser exposure to the eye directly. Other applications of the phototherapy apparatus 100 comprise cellulite reduction, skin rejuvenation, pain relief, fat reduction and/or contouring, laser acupuncture, wound healing, and/or pressure ulcer treatment.

In the foregoing specification, specific embodiments of the present invention have been described. However, one of ordinary skill in the art appreciates that various modifications and changes can be made without departing from the scope of the present invention as set forth in the claims below. For example, the therapeutic light source and the massage component are not limited to the presently disclosed forms. The massage component can take any other geometrical forms in addition to the spherical shape as disclosed. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A phototherapy apparatus for treatment of a biological tissue, the phototherapy apparatus comprising:
   at least one light source configured to provide therapeutic light to be absorbed by the biological tissue;
   a synthetic jet cooler configured for dissipating heat produced by said at least one light source; and at least one rolling massage ball transparent to the therapeutic light and configured to provide mechanical massage to the biological tissue, wherein said at least one light source is positioned external of and spaced apart from said rolling massage ball in an arrangement such that the therapeutic light can be transmitted from said at least one light source to an outer surface of said at least one rolling massage ball and through said at least one rolling massage ball and such that the therapeutic light and the mechanical massage can be applied to the biological tissue in a concerted manner.

2. The phototherapy apparatus of claim 1, wherein the at least one rolling massage ball has a diffusive optical surface capable of increasing a spread angle of the therapeutic light.

3. The phototherapy apparatus of claim 1, wherein the light source comprises a high power laser or a high power light emitting diode (LED).

4. The phototherapy apparatus of claim 1, wherein said at least one rolling massage ball is configured to rotate freely in all directions.

5. The phototherapy apparatus of claim 1, further comprising one or more optical elements disposed between said at least one light source and said at least one rolling massage ball, wherein said one or more optical elements are configured to affect the therapeutic light.

6. The phototherapy apparatus of claim 1, further comprising a display unit and control buttons.

7. The phototherapy apparatus of claim 1, further comprising a motor coupled to the at least one rolling massage ball and configured to generate a movement of the at least one rolling massage ball.

8. The phototherapy apparatus of claim 1, wherein a refractive index and a diameter of said at least one rolling massage ball are selected to shape the therapeutic light to a predetermined spot size.

9. A method for making a phototherapy apparatus for treatment of a biological tissue, the method comprising the steps of:

providing at least one light source configured to provide therapeutic light to be absorbed by the biological tissue;

providing a synthetic jet cooler configured for dissipating heat produced by said at least one light source; and providing at least one rolling massage ball transparent to the therapeutic light and configured to provide mechanical massage to the biological tissue, wherein said at least one light source is positioned external of and spaced apart from said rolling massage ball in an arrangement such that the therapeutic light can be transmitted from said at least one light source to an outer surface of said at least one rolling massage ball and through said at least one rolling massage ball and such that the therapeutic light and the mechanical massage can be applied to the biological tissue in a concerted manner.

10. The method of claim 9, wherein the at least one rolling massage ball has a diffusive optical surface capable of increasing a spread angle of the therapeutic light.

11. The method of claim 9, wherein the light source comprises a high power laser or a high power light emitting diode (LED).

12. A method for treatment of biological tissue with phototherapy, the method comprising the steps of:

providing at least one light source configured to provide therapeutic light to be absorbed by the biological tissue;

providing a synthetic jet cooler configured for dissipating heat produced by said at least one light source;

providing at least one rolling massage ball transparent to the therapeutic light and configured to provide mechanical massage to the biological tissue, wherein said at least one light source is positioned external of and spaced apart from said rolling massage ball in an arrangement such that the therapeutic light can be transmitted from said at least one light source to an outer surface of said at least one rolling massage ball and through said at least one rolling massage ball; and applying said rolling massage ball to the biological tissue such that the therapeutic light and the mechanical massage are applied to the biological tissue in a concerted manner.

13. The method of claim 12, wherein the light source comprises a high power laser or a high power light emitting diode (LED).

14. The method of claim 12, wherein the at least one rolling massage ball has a diffusive optical surface capable of increasing a spread angle of the therapeutic light.

15. The method of claim 12, wherein the mechanical massage causes a reduction in tissue thickness and an increase in tissue density to facilitate absorption or interaction of the therapeutic light with the biological tissue, and the therapeutic light stimulates inter or intra cellular response and increases micro-circulation of the biological tissue.

* * * * *